United States Patent
Niwa

(10) Patent No.: US 9,576,780 B2
(45) Date of Patent: Feb. 21, 2017

(54) MASS SPECTROMETER WITH TIMING DETERMINATION BASED ON A SIGNAL INTENSITY IN A CHROMATOGRAM

(75) Inventor: Akihiko Niwa, Tokorozawa (JP)

(73) Assignee: SHIMADZU CORPORATION, Kyoto (JP)

( * ) Notice: Subject to any disclaimer, the term of this patent is extended or adjusted under 35 U.S.C. 154(b) by 343 days.

(21) Appl. No.: 14/359,744

(22) PCT Filed: Nov. 22, 2011

(86) PCT No.: PCT/JP2011/076953
§ 371 (c)(1),
(2), (4) Date: Jun. 3, 2014

(87) PCT Pub. No.: WO2013/076826
PCT Pub. Date: May 30, 2013

(65) Prior Publication Data
US 2014/0339422 A1 Nov. 20, 2014

(51) Int. Cl.
*H01J 49/00* (2006.01)
*H01J 49/04* (2006.01)
(Continued)

(52) U.S. Cl.
CPC ........... *H01J 49/0081* (2013.01); *G01N 30/72* (2013.01); *G01N 30/8696* (2013.01);
(Continued)

(58) Field of Classification Search
CPC .. H01J 49/0081; H01J 49/0031; H01J 49/004; H01J 49/4265; G01N 30/72
See application file for complete search history.

(56) References Cited

U.S. PATENT DOCUMENTS

| 7,956,322 B2* | 6/2011 | Sugiyama | ........... H01J 49/0045 250/281 |
| 8,198,585 B2* | 6/2012 | Yamaguchi | ............ G01N 30/72 250/281 |

(Continued)

FOREIGN PATENT DOCUMENTS

| JP | 2001-249114 A | 9/2001 |
| JP | 2002-181784 A | 6/2002 |

(Continued)

OTHER PUBLICATIONS

Chinese Office Action issued Aug. 25, 2015 in Chinese Patent Application No. 201180075013.

(Continued)

*Primary Examiner* — Brooke Purinton
(74) *Attorney, Agent, or Firm* — Sughrue Mion, PLLC

(57) ABSTRACT

A mass spectrometer including chromatogram creation means for creating a chromatogram showing changes over time in an ion intensity within a predetermined mass range based on the MS analysis results, and timing determination means for determining a timing to perform MS/MS analysis based on the chromatogram. The timing determination means determines, as a timing to perform MS/MS analysis, a point in time at which a signal intensity in the chromatogram reaches a predetermined upper limit after exceeding a predetermined lower limit or a point in time at which a signal intensity in the chromatogram reaches a top of a peak without reaching the upper limit after exceeding the lower limit. It is thus possible to collect precursor ions at a timing at which the signal intensity of a peak originating from sample components is highest between the upper limit and lower limit, thereby obtaining a high quality MS/MS spectrum.

4 Claims, 5 Drawing Sheets

(51) Int. Cl.
*G01N 30/86* (2006.01)
*G01N 30/72* (2006.01)
*H01J 49/42* (2006.01)

(52) U.S. Cl.
CPC ........ *H01J 49/004* (2013.01); *H01J 49/0031* (2013.01); *H01J 49/4265* (2013.01)

(56) References Cited

U.S. PATENT DOCUMENTS

| | | | |
|---|---|---|---|
| 8,935,101 B2 * | 1/2015 | Wright | G01N 30/8675 250/281 |
| 9,431,224 B2 * | 8/2016 | Nakano | G01N 30/72 |
| 2001/0007349 A1 | 7/2001 | Nagai | |
| 2002/0074490 A1 | 6/2002 | Umemura | |

FOREIGN PATENT DOCUMENTS

| | | | |
|---|---|---|---|
| JP | 2007-198882 A | 8/2007 | |
| JP | 2010-019655 A | 1/2010 | |

OTHER PUBLICATIONS

Japanese Office Action issued Dec. 16, 2014 in Japanese Patent Application No. 2013-545701.
International Search Report for PCT/JP2011/076953 dated Feb. 28, 2012.
Communication from the European Patent Office dated Apr. 16, 2015 in International Application No. PCT/JP2011/076953.

* cited by examiner

MASS SPECTROMETER WITH TIMING DETERMINATION BASED ON A SIGNAL INTENSITY IN A CHROMATOGRAM

CROSS REFERENCE TO RELATED APPLICATIONS

This application is a National Stage of International Application No. PCT/JP2011/076953 filed Nov. 22, 2011, the contents of all of which are incorporated herein by reference in their entirety.

TECHNICAL FIELD

The present invention relates to a mass spectrometer that sequentially ionizes and mass analyzes sample components which have been temporally separated by a column of a liquid chromatograph or a gas chromatograph. More particularly, it relates to a mass spectrometer having an MS/MS (=$MS^2$) analysis function which fragments ions having a specific mass (m/z, to be exact) as precursor ions and mass analyzes product ions generated by the fragmentation.

BACKGROUND ART

In the case of a gas chromatograph mass spectrometer (GC/MS) or a liquid chromatograph mass spectrometer (LC/MS), sample components which have been temporally separated by a column of a GC or an LC are introduced in sequence into the mass spectrometer (MS), and each component is ionized, respectively, and thereafter subjected to mass separation and detection. In this case, a mass spectrum can be created by focusing on a specific time, and assigning the mass to the horizontal axis and the intensity to the vertical axis. Further, a chromatogram (mass chromatogram) can be created by focusing on a specific mass, and assigning the time to the horizontal axis and the intensity to the vertical axis. Still further, a three-dimensional chromatogram can also be created by combining these and adopting the time, the intensity (ion intensity) and the mass as the three axes.

As the mass spectrometer (MS) for such GC/MS and LC/MS, $MS^n$ (where n is an integer equal to or larger than two) mass spectrometers that fragment ions having a specific mass as precursor ions and mass analyze product ions generated by the fragmentation are sometimes used. The $MS^n$ mass spectrometers include a mass spectrometer equipped with an automatic $MS^n$ analysis function that automatically selects precursor ions based on the results of $MS^{n-1}$ analysis and performs $MS^n$ analysis (for example, refer to JP 2010-19655 A).

In a GC/MS or LC/MS in which such a mass spectrometer having an automatic $MS^n$ analysis function is used, for example, a chromatogram or chromatograms on one or a plurality of masses is progressively created while continually introducing the eluate from the column of the GC or LC and repeatedly performing MS (=$MS^1$) analysis. Then, at a point in time at which a signal intensity in the chromatogram satisfies a predetermined condition, for example, a point in time at which the signal intensity exceeds a predetermined threshold as indicated by t1 and t2 in FIG. 6, ions having a mass corresponding to the chromatogram or chromatograms are collected as precursor ions and MS/MS analysis is performed. In order to obtain MS/MS spectra with a high S/N ratio, it is preferable to collect as large amount of precursor ions as possible. For that purpose, a method is available, as shown in FIG. 7, in which precursor ions are collected after a peak top of a chromatogram appears since exceeding the threshold.

BACKGROUND ART DOCUMENT

Patent Document

[Patent Document 1] JP 2010-19655 A

DISCLOSURE OF THE INVENTION

Problems to be Solved by the Invention

As previously described, to obtain MS/MS spectra having a high S/N ratio, it is desirable to collect and perform MS/MS analysis on as large amount of precursor ions as possible. However, on the other hand, in the case of a mass spectrometer, such as a quadrupole mass filter or a three-dimensional quadrupole ion trap, if the amount of introduced ions is too large, the mass separation performance will deteriorate in some cases due to the influence of the space-charge effect and consequently it is not possible to obtain high-quality MS/MS spectra.

The present invention has been developed to solve the aforementioned problem, and the objective is to enable performing a MS/MS analysis with an appropriate amount of precursor ions in a mass spectrometer that is used in combination with a chromatograph and is capable of automatically performing MS/MS analysis including selection and fragmentation of precursor ions.

Means for Solving the Problems

To solve the aforementioned problems, a mass spectrometer according to the present invention sequentially introduces sample components which are temporally separated by a column of a chromatograph into an ionization unit and performs mass analysis, the mass spectrometer including:

a) MS analysis performing means for repeatedly performing MS analysis on ions generated in the ionization unit;

b) chromatogram creation means for creating a chromatogram that shows changes over time in an ion intensity within a predetermined mass range based on a result of the MS analysis;

c) timing determination means for determining a timing to perform MS/MS analysis based on a signal intensity in the chromatogram; and d) MS/MS analysis performing means for performing MS/MS analysis in which ions belonging to the mass range among ions generated in the ionization unit are adopted as precursor ions in accordance with the timing to perform MS/MS analysis determined by the timing determination means, wherein:

the timing determination means determines, as the timing to perform MS/MS analysis, a point in time at which a signal intensity in the chromatogram reaches a predetermined upper limit after exceeding a predetermined lower limit, or a point in time at which, after exceeding the lower limit, a signal intensity in the chromatogram arrives at a top of a peak without reaching the upper limit.

The upper limit and the lower limit used by the timing determination means may be values that are preset in the mass spectrometer or may be values that a user can arbitrarily enter and set. Another configuration may also be adopted in which, upon entering and setting analysis conditions for the chromatograph and/or the mass spectrometer by a user, an appropriate upper limit and lower limit in accordance with the analysis conditions are automatically set on the apparatus side.

The mass range to be taken for creating the chromatogram may be a value that is preset in the mass spectrometer. It is desirable to adopt another configuration, for example, in which a user is allowed to set an arbitrary mass range. It should be noted that the mass range can be a mass at only one point, or otherwise an entire mass range of the analysis in the MS analysis.

In a case where a plurality of ions can be selected as precursor ions for MS/MS analysis at the timing to perform MS/MS analysis determined as described above, that is, in a case where, as a result of the MS analysis, a plurality of ions are detected within the mass range at a time that corresponds to the timing to perform MS/MS analysis, the MS/MS analysis performing means further determines which ions among the plurality of ions are to be set as precursor ions and in which order to set the ions as the precursor ions to perform the MS/MS analysis. For example, all (or only a predetermined number) of the plurality of ions can be selected in descending order or ascending order of peak intensity or in ascending order or descending order of mass and the MS/MS analysis can be performed sequentially, or only ions that satisfy a predetermined criterion (for example, ions for which the peak intensity is equal to or greater than a predetermined lower limit, or ions for which the peak intensity falls between a predetermined lower limit and upper limit) among the plurality of ions can be selected and the MS/MS analysis is performed in a predetermined order. It should be noted that, when a plurality of ions can be selected as precursor ions in this manner, a rule which ions are to be set as precursor ions and in which order to set the ions as the precursor ions to perform MS/MS analysis may be determined in advance for the apparatus, or a configuration may be adopted so that the user can previously set which ions are to be set as precursor ions and which order to set the ions in as one of the analysis conditions.

It is preferable, in the mass spectrometer according to the present invention, that:

the chromatogram creation means may create a plurality of chromatograms relating to a predetermined plurality of mass ranges;

the timing determination means may determine, as the timing to perform the MS/MS analysis, a point in time at which at least any one signal intensity of the plurality of chromatograms reaches a predetermined upper limit after exceeding a predetermined lower limit or a point in time at which the at least any one signal intensity reaches a top of a peak without reaching the upper limit after exceeding the lower limit; and the MS/MS analysis performing means may perform MS/MS analysis that, among ions generated in the ionization unit, takes ions belonging to a mass range corresponding to a chromatogram that is used by the timing determination means as precursor ions.

Effects of the Invention

According to the mass spectrometer having the aforementioned configurations according to the present invention, a timing at which a signal intensity in the chromatogram is largest between the lower limit and the upper limit is determined as a timing to perform MS/MS analysis, and the collection of precursor ions for the MS/MS analysis can be performed in accordance with the timing. It is thereby possible to perform MS/MS analysis on an optimal amount of precursor ions, and obtain higher quality MS/MS spectra in comparison to the conventional technology.

BEST MODES FOR CARRYING OUT THE INVENTION

A liquid chromatograph/ion trap time-of-flight mass spectrometer (LC/IT-TOFMS) that is one embodiment of the present invention is now be described in detail using FIG. 1 to FIG. 4.

Figure 1:
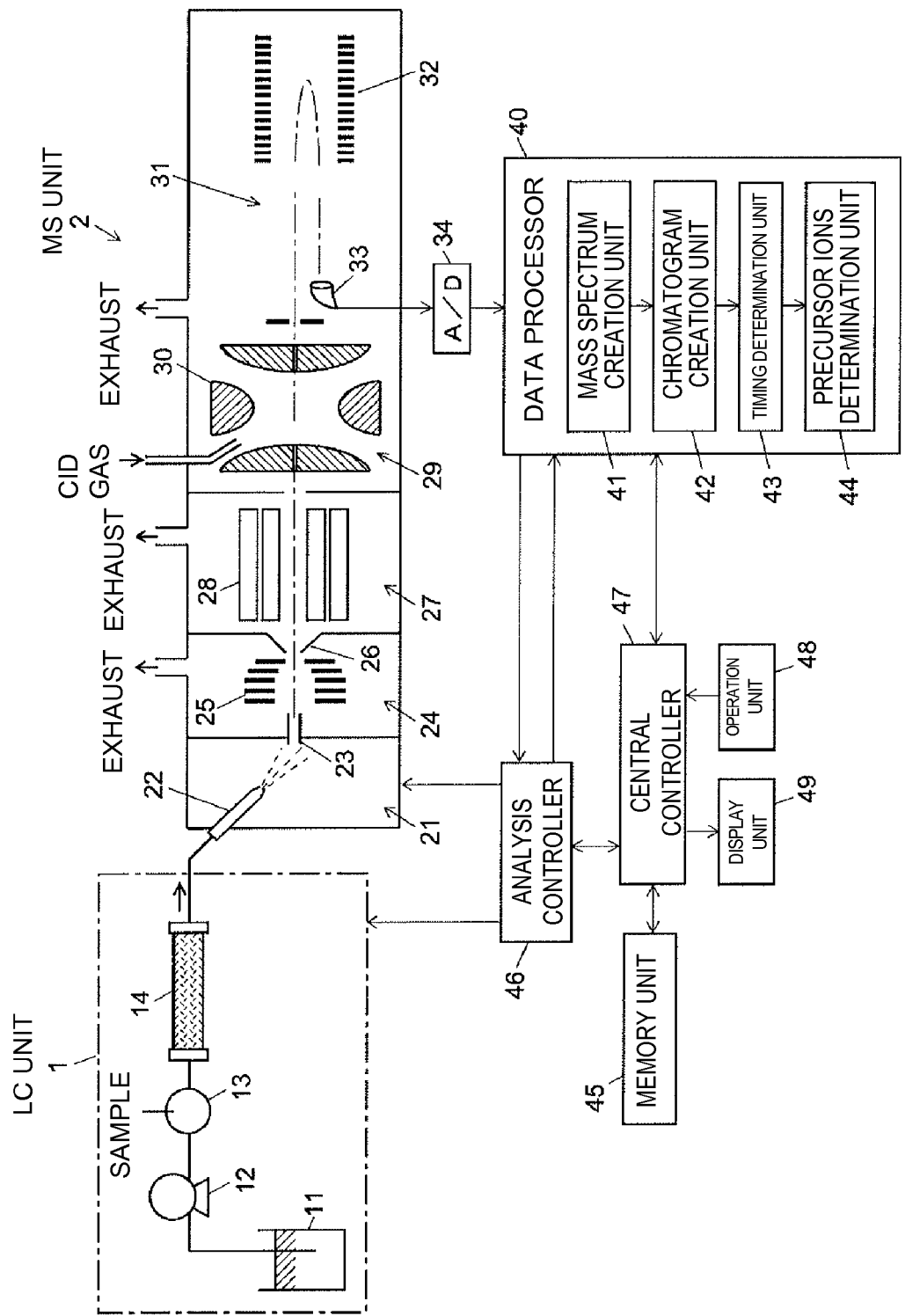
FIG. 1 is a schematic configuration diagram of an LC/IT-TOFMS according to an embodiment of the present invention.

FIG. 1 is a configuration diagram of the main portion of the LC/IT-TOFMS of the present embodiment. This LC/IT-TOFMS roughly includes a liquid chromatograph (LC) unit 1 and a mass spectrometer (MS) unit 2. An electrospray ionization (ESI) interface is used as an atmospheric pressure ionization interface which connects the LC unit 1 and the MS unit 2. It should be noted that the ionization method is not limited to it, and various other kinds of ionization interfaces such as, for example, an atmospheric pressure chemical ionization (APCI) method or an atmospheric pressure photoionization (APPI) method can be used.

A liquid sending pump 12 provided in the liquid chromatograph (LC) unit 1 draws a mobile phase held in a mobile phase container 11 and sends it to a column 14 through an injector 13 at a constant flow rate. The injector 13 has an auto sampler, and automatically selects a pre-prepared sample and injects a predetermined amount of the sample into the mobile phase at a predetermined timing. When the sample is injected into the mobile phase by the injector 13, the sample is introduced into the column 14 by the flow of the mobile phase. While passing through the column 14, various components in the sample are separated and eluted from the outlet of the column 14 with time differences. Then, they are introduced to the MS unit 2.

The MS unit 2 has an ionization chamber 21 (corresponds to "ionization unit" in the present invention) which is kept at an atmospheric atmosphere, and an analysis chamber 29 which is vacuum-evacuated by a turbo molecular pump (not shown) to be kept at a high vacuum atmosphere. Between these chambers, a first-stage intermediate vacuum chamber 24 and a second-stage intermediate vacuum chamber 27 are provided between which the degree of vacuum is increased in a stepwise manner. The ionization chamber 21 communicates with the first-stage intermediate vacuum chamber 24 via a thin desolvation pipe 23, and the first-stage intermediate vacuum chamber 24 communicates with the second-stage intermediate vacuum chamber 27 via a small-sized orifice bored on top of a conical skimmer 26.

When the eluate including the sample components provided from the LC unit 1 reaches an ESI nozzle 22 which serves as an ion source, electric charges are given to the eluate by a direct-current high voltage applied by a high-voltage power supply (not shown) and the eluate is sprayed into the ionization chamber 21 as charged small droplets. The charged droplets collide with atmospherically derived gas molecules to be broken into smaller droplets, which are promptly dried (or desolvated) and the sample molecules vaporize. The sample molecules are ionized by ion evaporation. The fine droplets including the generated ions are sucked into the desolvation pipe 23 by the pressure difference, and while they pass through the desolvation pipe 23, the desolvation process further progresses to generate more ions. While being converged by ion guides 25 and 28, the ions pass through the two intermediate vacuum chambers 24 and 27 to be sent into the analysis chamber 29. In the analysis chamber 29, the ions are introduced to the inside of a three-dimensional quadrupole ion trap 30.

In the ion trap 30, the ions are temporarily captured and stored by a quadrupole electric field formed by a radio-frequency voltage which is applied to each electrode from a power source (not shown). At a predetermined timing, a kinetic energy is collectively provided to the variety of ions stored inside the ion trap 30, and the ions are expelled from the ion trap 30 toward a time-of-flight mass separator (TOF) 31, which serves as a mass separator. That is, the ion trap 30 is the starting point of the flight of the ions toward the TOF 31. The TOF 31 has a reflectron electrode 32 to which a direct-current voltage is applied from a direct-current power source (not shown). By the action of the direct-current electric field formed by the reflectron electrode 32, the ions return and reach an ion detector 33 as a detector. Although the ions are collectively ejected from the ion trap 30, since ions having smaller mass (m/z, to be exact) fly faster, they reach the ion detector 33 with time differences according to their m/z. The ion detector 33 sequentially outputs an electric current as a detection signal in accordance with the number of arrived ions.

This detection signal is converted into a digital value by an A/D converter 34, and then provided to a data processor 40. At the data processor 40, a mass spectrum creation unit 41 measures the signal intensity of ions every time point from the point in time when the ions have been collectively ejected from the ion trap 30 to the point in time when all of the ions reach the ion detector 33. The mass spectrum creation unit 41 converts the time information into mass information, and creates a mass spectrum in which the mass is assigned to the horizontal axis and the signal intensity to the vertical axis. To achieve the characteristic operations of the present embodiment, in addition to the mass spectrum creation unit 41, the data processor 40 includes a chromatogram creation unit 42, a timing determination unit 43, and a precursor ions determination unit 44 as function blocks.

Based on instructions from a central controller 47, an analysis controller 46 controls the operations of each element of the LC unit 1 and the MS unit 2 to perform separation of the sample by means of the LC unit 1 and an MS analysis or MS/MS analysis by means of the MS unit 2. An operation unit 48 and a display unit 49 as a user interface are connected to the central controller 47. In response to an operation by an operator through the operation unit 48, the central controller 47 provides a variety of instructions for analysis to the analysis controller 46 and the data processor 40, and outputs an analysis result such as a mass spectrum and a chromatogram to the display unit 49. A memory unit 45 that stores a large amount of data that is collected by the MS unit 2 and setting information that is entered from the operation unit 48 and the like is also connected to the central controller 47. The central controller 47, the analysis controller 46, and the data processor 40 can be realized by, for example, a personal computer in which predetermined control/processing software is installed. In the present embodiment, the ion trap 30, the TOF 31, and the analysis controller 46 work together and serve as the MS analysis performing means and the MS/MS analysis performing means in the present invention.

As shown in the drawing, the ion trap 30 is configured to be capable of supplying, for example, a collision-induced dissociation (CID) gas such as argon, and ions that are stored in the ion trap 30 can be fragmented by CID to generate product ions. When performing MS/MS analysis, after first storing a variety of ions that were generated in the ionization chamber 21 in the ion trap 30, a voltage that is applied to each electrode of the ion trap 30 is controlled so that only ions having a specific mass among the stored ions are selectively retained as precursor ions, and thereafter a CID gas is introduced into the ion trap to fragment the precursor ions. The product ions generated in this manner are collectively ejected from the ion trap 30 towards the TOF 31, and by separating and detecting the product ions for each mass, a mass spectrum of the product ions, that is, an MS/MS spectrum can be obtained.

Figure 2:
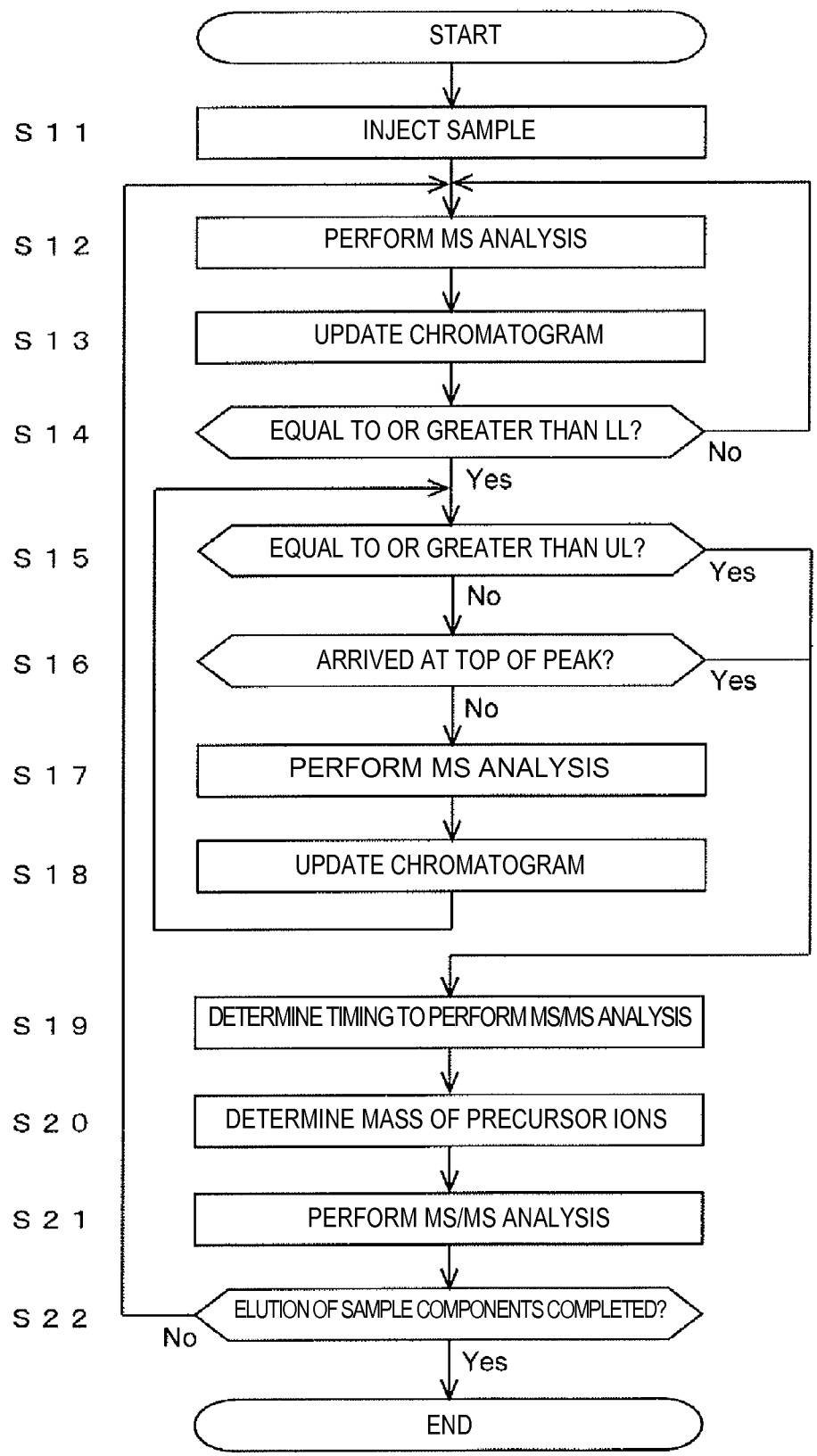
FIG. 2 is a flowchart showing an example of analysis procedures according to the embodiment of the present invention.
Figure 3:
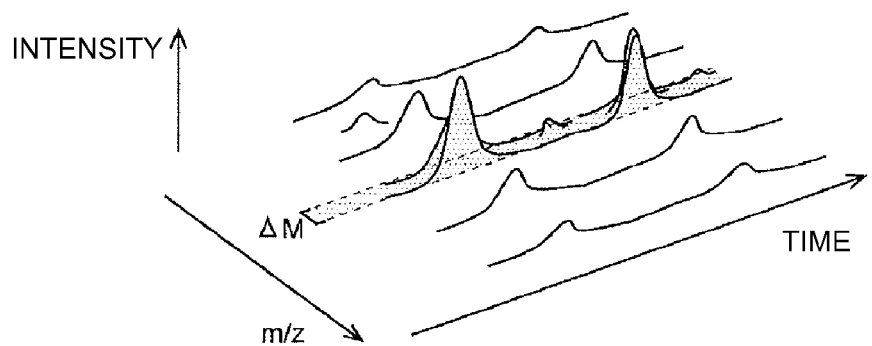
FIG. 3 schematically shows three-dimensional data that is collected according to the embodiment of the present invention.

Characteristic operations of the LC/IT-TOFMS having the above described configuration is now be described referring to FIG. 2 to FIG. 4. FIG. 2 is a flowchart showing control and processing procedures of the LC/IT-TOFMS according to the present embodiment.

When an operator enters and sets analysis conditions from the operation unit 48 and then instructs the performance of automatic analysis, first, the central controller 47 that receives this instruction provides the analysis controller 46 with an instruction to perform LC/MS analysis of a target sample that is prepared in the injector 13. The analysis controller 46 controls the LC unit 1 and the MS unit 2, respectively, in accordance with the instruction from the central controller 47. As a result, the target sample is injected into the mobile phase from the injector 13 (step S11) and thereby sent to the column 14, and the eluate is supplied from the column 14 is introduced to the MS unit 2. The MS unit 2 repeatedly performs mass analysis that takes the eluate that is sequentially introduced as a target (step S12). It should be noted that, in this step, mass analysis (that is, MS analysis) is performed in which selection and fragmentation of ions is not performed.

A detection signal that is obtained with the ion detector 33 through the aforementioned MS analysis is sent to the mass spectrum creation unit 41 of the data processor 40 through the A/D converter 34. At the mass spectrum creation unit 41, a mass spectrum over a predetermined mass range is created in accordance with a single ejection of ions from the ion trap 30. By repeatedly performing MS analysis and creation of a mass spectrum in this manner as time elapses, the data processor 40 obtains three-dimensional data having the three dimensions of mass (m/z), intensity, and time as shown in FIG. 3, and the three-dimensional data is stored in the memory unit 45.

The chromatogram creation unit 42 extracts a previously set mass range (ΔM in FIG. 3) from the three-dimensional data stored in the memory unit 45, sums up the intensity data in the mass (m/z) axis direction, and converts the three-dimensional data to two-dimensional data in which time is assigned to the horizontal axis and intensity is assigned to the vertical axis. This is a chromatogram (mass chromatogram) that corresponds to the mass range ΔM. This chromatogram is updated in real time by the chromatogram creation unit 42, that is, every time that new data is input from the MS unit 2, the chromatogram is updated so as to add a curve that corresponds to the new data (step S13). FIG. 4 illustrates an example of the chromatogram.

A mass (that is, the width of ΔM) to be taken as an object for creation of the chromatogram may be previously determined for the apparatus, or a configuration may be adopted that allows the user (a person in charge of the analysis) to set the mass as one of the analysis conditions. It should be noted that the aforementioned ΔM may be a certain single mass, and in such case summing-up processing is not required.

In a case where the mass of ions to be adopted as precursor ions for MS/MS analysis is previously decided, the chromatogram creation unit 42 generates only a chromatogram for the mass. In other cases, the chromatogram creation unit 42 creates a chromatogram (a so-called "total ion chromatogram") relating to the entire mass range to be analyzed in the MS analysis by the MS unit 2, or divides the mass range into a plurality of sections and creates a chromatogram (mass chromatogram) over the mass range corresponding to each section in real time, respectively.

Figure 4:
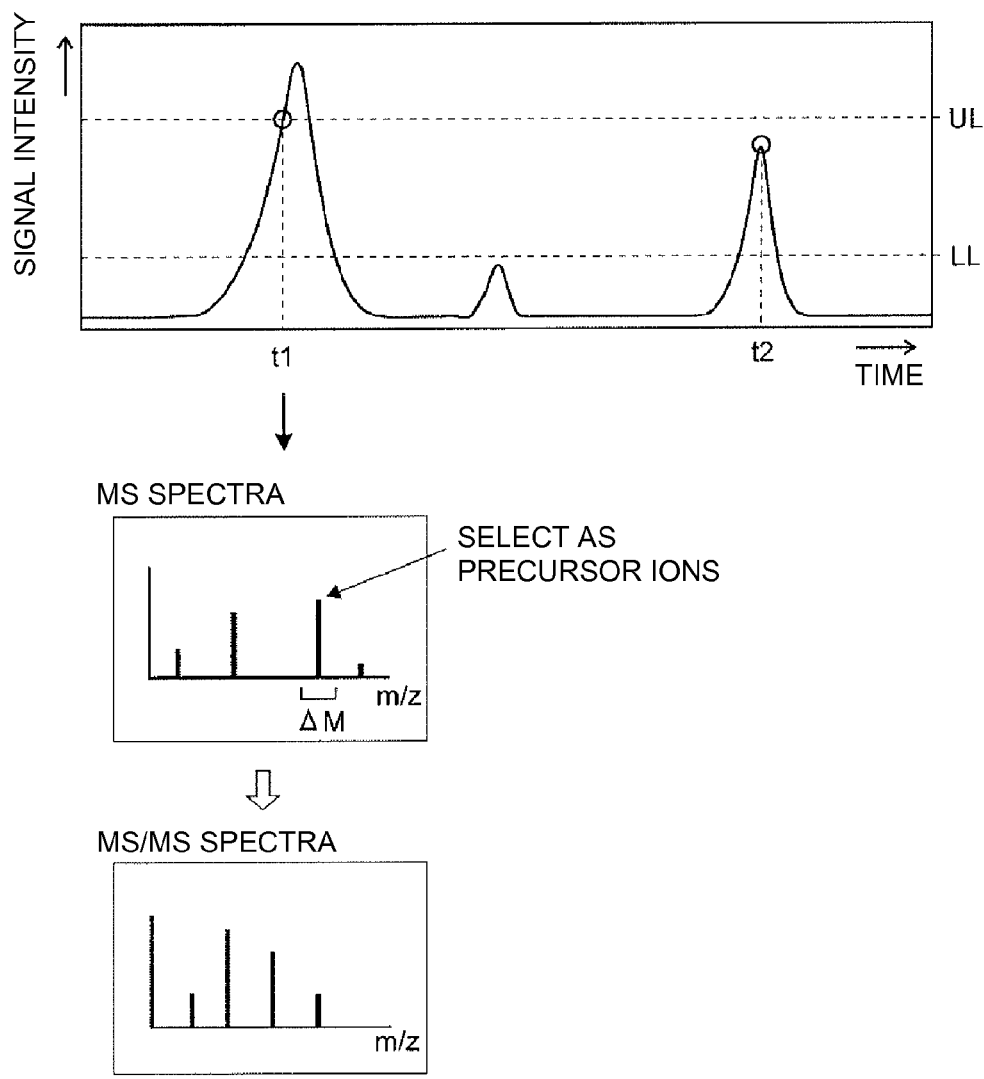
FIG. 4 is a multi-view drawing for explaining a method for determining a timing at which to perform MS/MS analysis according to the embodiment of the present invention.

When there are no sample components in the eluate from the column 14, the signal intensity of the chromatogram is maintained at substantially zero (or baseline), and when sample components start to flow out at a certain point in time, the signal intensity of a chromatogram corresponding to them begins to rise (refer to FIG. 4). The timing determination unit 43 constantly monitors the latest intensity data (signal intensity) for one or a plurality of chromatograms created by the chromatogram creation unit 42, and sequentially determines whether or not the intensity data conforms with a previously set condition. At a point in time at which the timing determination unit 43 determines that the intensity of any of the chromatograms satisfies the condition, ions corresponding to the chromatogram are collected as precursor ions and MS/MS analysis is performed. By automatically collecting precursor ions and performing MS/MS analysis based on chromatograms in this manner, for a single injection of a sample at the LC unit 1, it is possible to capture ions that originate from a target component at a timing at which the target component is eluted from the column 14, and automatically obtain an MS/MS spectrum in which the structure and composition of the component is reflected.

A feature of the liquid chromatograph mass spectrometer of the present embodiment is a timing determination operation that is performed in the timing determination unit 43 when determining the timing for collecting precursor ions for MS/MS analysis from a chromatogram that is obtained by MS analysis as described above. This feature is described in detail hereunder. In the case of performing an operation to determine the timing for collecting precursor ions by means of the timing determination unit 43, the user enters determination conditions in advance from the operation unit 48 and stores the determination conditions in the memory unit 45. Here, as one of the determination conditions, an upper limit UL and a lower limit LL (where UL>LL) of the signal intensity can be set as a pair.

The timing determination unit 43 sequentially compares the latest intensity data of one or a plurality of chromatograms that are continuously created by the chromatogram creation unit 42 by repeating MS analysis at the MS unit 2, and the lower limit LL. When the signal intensity exceeds the lower limit LL, the timing determination unit 43 determines the point in time as being the starting point of a peak relating to the sample components. When a further period of time elapses and the signal intensity reaches the upper limit UL, the timing determination unit 43 determines that point in time as a timing to perform MS/MS analysis (that is, timing for collection of precursor ions). Further, in a case where the signal intensity reaches the top of a peak without arriving at the upper limit UL after exceeding the lower limit LL, the timing determination unit 43 determines that point in time as a timing for collection of precursor ions. That is, in the case of the chromatogram shown in FIG. 4, a time t1 and a time t2 are each a timing for collection of precursor ions. It should be noted that, a determination as to whether or not the top of a peak has been reached can be made utilizing a known method. For example, a change in the signal intensity (that is, the slope of the chromatogram waveform) can be examined, and a point in time at which the slope turns from a positive slope into a negative slope can be determined as being the position of the top of the peak.

The procedure for the determination by the timing determination unit 43 described above is now be described referring to the flowchart shown in FIG. 2. First, each time a chromatogram is updated, the timing determination unit 43 compares the latest intensity data for the chromatogram and the lower limit LL, and determines whether or not the signal intensity is equal to or greater than the lower limit LL (step S14). If the signal intensity is less than the lower limit LL (No in step S14), the operation returns to step S12 to repeat performance of MS analysis and a similar determination. On the other hand, if the signal intensity is equal to or greater than the lower limit LL (Yes in step S14), the timing determination unit 43 then determines whether or not the signal intensity is equal to or greater than the upper limit UL (step S15). If the signal intensity is less than the upper limit UL (No in step S15), the timing determination unit 43 then determines whether or not the top of a peak has been reached in the chromatogram (step S16). If the top of a peak has not been reached in the chromatogram (No in step S16), MS analysis is performed again (step S17), the chromatogram is updated (step S18), and the operation returns to step S15. On the other hand, if the signal intensity is equal to or greater than the upper limit UL (Yes in step S15), or if the top of a peak was reached in the chromatogram (Yes in step S16), the timing determination unit 43 determines that point in time as a timing to perform MS/MS analysis (step S19).

Although in the above described example a configuration is adopted in which the chromatogram is updated each time MS analysis is performed one time, and a determination by the timing determination unit 43 is performed (step S14, or steps S15 and S16) each time the chromatogram is updated one time, the present invention is not limited to it, and a configuration may also be adopted so as to update a chromatogram each time MS analysis has been performed a plurality of times or so that the timing determination unit 43 performs a determination each time a chromatogram has been updated a plurality of times.

When a timing to perform MS/MS analysis has been determined by the above described process, next, among the ions that are detected by the MS unit 2 at a time that is determined as the timing to perform MS/MS analysis, the precursor ions determination unit 44 determines the ions belonging to the mass range ΔM that corresponds to the chromatogram used for the timing determination (that is, the chromatogram that satisfied the above described predetermined determination condition) as the precursor ions for MS/MS analysis (step S20). More specifically, the precursor ions determination unit 44 obtains a mass spectrum (MS spectrum) at a time that is determined as the timing to perform MS/MS analysis, for example, t1, from the memory unit 45, and determines a mass corresponding to a peak that appears within the mass range ΔM in the MS spectrum as the mass of the precursor ions. At this time, if there is a plurality of peaks within the mass range ΔM, a peak that satisfies a predetermined condition, for example, a mass which gives the highest peak intensity within the aforementioned ΔM is taken to be the mass of the precursor ions.

When the mass of the precursor ions is determined, a timing signal that indicates a timing to perform MS/MS analysis and information of the mass of the precursor ions is sent to the central controller 47 from the data processor 40. As soon as the central controller 47 receives the timing signal, the central controller 47 provides the analysis controller 46 with an instruction to collect ions of the aforementioned mass and perform MS/MS analysis, and in response thereto the analysis controller 46 controls the MS unit 2 (step S21). It should be noted that, in the above described example, at the time when the timing to perform MS/MS analysis, for example, the time t1 shown in FIG. 4, is determined by the timing determination unit 43, the time t1 in principle has already passed, and the ions detected by the MS unit 2 at the time t1 are not present in the ion trap 30. Therefore, in practice, MS/MS analysis (that is, selection of a mass of ions and fragmentation of the selected ions in the ion trap 30, mass separation by the TOF 31 of various product ions generated by the fragmentation, and detection by the ion detector 33) is performed with respect to ions that are captured and stored in the ion trap 30 immediately after the time t1.

When the MS/MS analysis is completed, the central controller 47 determines whether or not elution of sample components from the column 14 is completed (step S22). Whether or not the elution is completed can be determined, for example, according to whether or not a predetermined time period has elapsed since the sample was injected in the above described step S11. Here, if it is determined that elution is not completed (No in step S22), the operation returns again to step S12 to perform MS analysis on the eluate from the column 14, and repeatedly perform steps S12 to S22 until elution of the sample components is completed (that is, until the result in step S22 is Yes).

As described above, according to the mass spectrometer of the present embodiment, by performing a determination based on two thresholds (the upper limit UL and the lower limit LL) with respect to a chromatogram obtained by MS analysis, precursor ions for use in MS/MS analysis can be collected at a timing at which a signal intensity of a peak originating from sample components is highest between the two thresholds. Since it is thereby possible to supply an amount of precursor ions that is as large as possible within a range in which the mass separation performance does not decline for MS/MS analysis, it is possible to obtain MS/MS spectra of a higher quality than in the conventional mass analysis that includes an automatic MS/MS analysis function.

Figure 5:
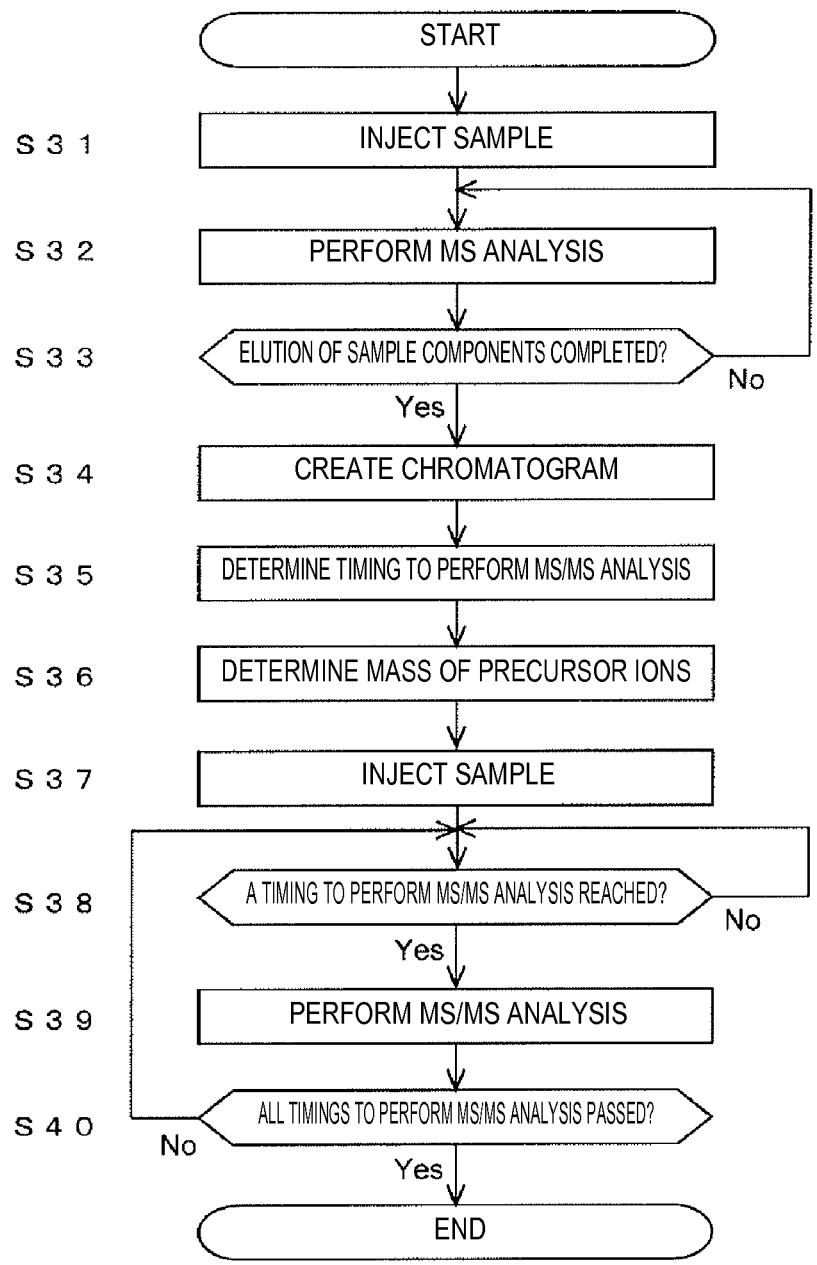
FIG. 5 is a flowchart showing another example of analysis procedures according to the embodiment of the present invention.
Figure 6:
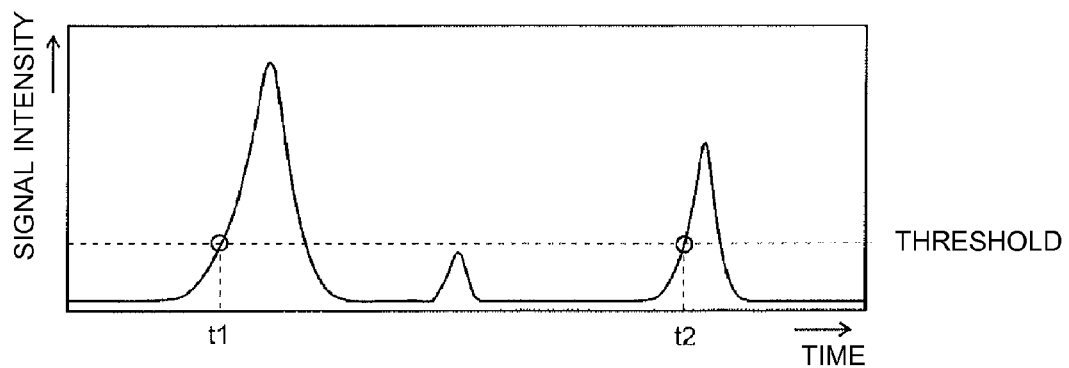
FIG. 6 is a drawing for explaining an example of a conventional method for determining a timing at which to perform MS/MS analysis.
Figure 7:
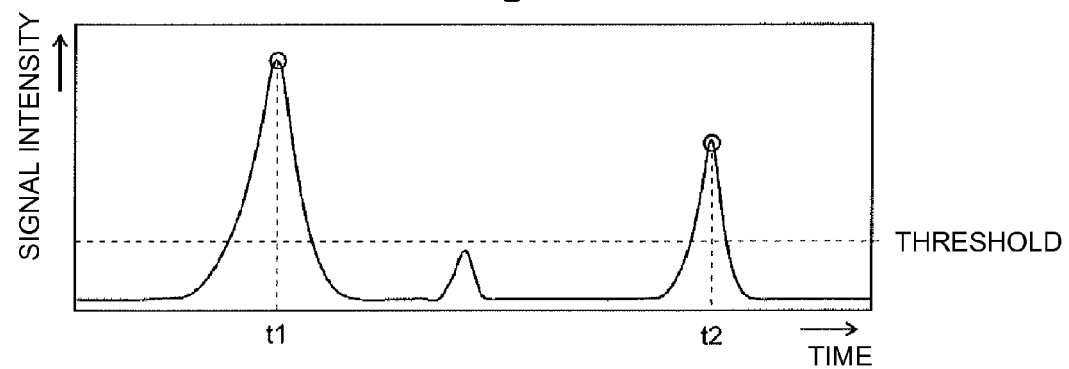
FIG. 7 is a drawing for explaining another example of the conventional method for determining a timing at which to perform MS/MS analysis.

Although in the above described example a configuration is adopted in which both MS analysis and MS/MS analysis are performed with respect to a single injection of a sample at the LC unit 1, the present invention is not limited to this. For example, a configuration may also be adopted in which the same sample is introduced twice to the LC unit 1 and only MS analysis is performed the first time the sample is introduced, and a timing to perform MS/MS analysis and the mass of the precursor ions is determined based on the MS analysis result. Subsequently, when the sample is introduced the second time, MS/MS analysis is performed at the determined timing to perform MS/MS analysis by taking ions of the determined mass as the precursor ions. The operations in this case is now be described using the flowchart in FIG. 5.

In this example, first, the target sample in injected into the mobile phase from the injector 13 of the LC unit 1 (step S31), and MS analysis is repeatedly performed with respect to the eluate from the column 14 until elution of the sample components is completed (steps S32 and S33). After elution of the sample components is completed (that is, when the result in step S33 is Yes), the chromatogram creation unit 42 creates a chromatogram relating to a predetermined one or plurality of mass ranges based on the results of the MS analysis (step S34).

Next, the timing determination unit 43 determines a timing to perform MS/MS analysis based on the chromatogram (step S35). More specifically, the timing determination unit 43 searches for a point at which the signal intensity in the chromatogram arrives at the upper limit UL after exceeding the lower limit LL or for a point at which the signal intensity in the chromatogram reaches the top of a peak without arriving at the upper limit UL after exceeding the lower limit LL, and determines a time corresponding to the location as a timing to perform MS/MS analysis.

Next, the precursor ions determination unit 44 reads a mass spectrum for each time that was determined as a timing to perform MS/MS analysis from the memory unit 45, and in the mass spectrum, determines the mass of a peak that appears within a mass range ΔM corresponding to the chromatogram used for determining the timing to perform the MS/MS analysis as the mass of the precursor ions at the timing to perform the MS/MS analysis (step S36). The one or a plurality of timings to perform MS/MS analysis and the information regarding the mass of precursor ions at the respective timings which are determined by the above described process are associated with each other and stored in the memory unit 45.

Subsequently, the same sample as that used in the above described step S31 is again injected into the mobile phase from the injector 13 (step S37). Thereafter, at a point in time at which a time stored in the memory unit 45 as a timing to perform MS/MS analysis comes (that is, a point in time at which the result in step S38 was Yes), ions having a mass that corresponds to the timing to perform the MS/MS analysis are collected in the ion trap 30 and MS/MS analysis is performed that uses these ions as precursor ions (step S39). Further, MS/MS analysis is performed each time that a time stored in the memory unit 45 as a timing to perform MS/MS analysis comes after that (steps S38 and S39), and the series of analysis is completed at a point in time at which MS/MS analysis is completed with respect to all the timings at which to perform MS/MS analysis (that is, a point in time at which the result in step S40 is Yes).

Implementation modes for the present invention have until now been described by using the embodiments. It should be noted that the present invention is not limited to the aforementioned embodiments, and appropriate changes made within the spirit of the present invention are allowed.

The present invention can also be applied to a mass spectrometer that uses another mass separator other than a time-of-flight mass separator, and for example, the present invention can also be applied to a mass spectrometer that uses a quadrupole mass filter. It is also possible to use a collision cell that includes quadrupole or multipole rods to which a radio-frequency voltage is applied instead of a three-dimensional quadrupole ion trap. In this case, because it is necessary to perform selection of precursor ions at a stage before the collision cell, a triple-quadrupole MS/MS mass spectrometer may be used as a typical example. Further, a configuration can also be adopted that uses a gas chromatograph (GC) instead of the above described LC unit 1.

EXPLANATION OF NUMERALS

1 . . . LC Unit
13 . . . Injector
14 . . . Column
2 . . . MS Unit
21 . . . Ionization Chamber
29 . . . Analysis Chamber
30 . . . Ion Trap
31 . . . TOF
33 . . . Ion Detector
34 . . . A/D Converter
40 . . . Data Processor
41 . . . Mass Spectrum Creation Unit
42 . . . Chromatogram Creation Unit
43 . . . Timing Determination Unit
44 . . . Precursor Ions Determination Unit
45 . . . Memory Unit
46 . . . Analysis Controller
47 . . . Central Controller
48 . . . Operation Unit
49 . . . Display Unit

The invention claimed is:

1. A mass spectrometer which sequentially introduces sample components which are temporally separated by a column of a chromatography into an ionization unit and performs mass analysis, comprising:
  a) mass spectrometry (MS) analyzer for repeatedly performing MS analysis on ions generated in the ionization unit; and
  a processor including
  b) chromatogram creation unit for creating a chromatogram that shows changes over time in an ion intensity within a predetermined mass range based on a result of the MS analysis; and
  c) timing determination unit for determining a timing to perform MS/MS analysis based on a signal intensity in the chromatogram;
  wherein the MS analyzer performs MS/MS analysis in which ions belonging to the mass range among ions generated in the ionization unit are adopted as precursor ions, in accordance with the timing to perform MS/MS analysis that is determined by the timing determination unit, wherein:
  the processor is configured to cause, when a signal intensity in the chromatogram reaches a predetermined upper limit after exceeding a predetermined lower limit, the timing determination unit to determine that point in time as the timing to perform MS/MS analysis, and when, after exceeding the lower limit, a signal intensity in the chromatogram arrives at a top of a peak without reaching the upper limit, the timing determination unit to determine that point in time as the timing to perform MS/MS analysis.

2. The mass spectrometer according to claim 1, further comprising:
  e) an operation unit for allowing a user to enter and set the upper limit and the lower limit.

3. The mass spectrometer according to claim 1 wherein:
  the chromatogram creation unit creates a plurality of chromatogram relating to a predetermined plurality of mass ranges;
  the processor is configured to cause, when at least any one signal intensity of the plurality of chromatograms reaches the predetermined upper limit after exceeding the predetermined lower limit, the timing determination unit to determine that point in time as the timing to perform MS/MS analysis for the respective mass range, and when the at least any one signal intensity reaches a top of a peak without reaching the upper limit after exceeding the lower limit, the timing determination unit to determine that point in time as the timing to perform MS/MS analysis for the respective mass range; and
  the MS analyzer performs MS/MS analysis that, among ions generated in the ionization unit, takes ions belonging to a mass range corresponding to a chromatogram that is used by the timing determination unit as precursor ions.

4. The mass spectrometer according to claim 2 wherein:
  the chromatogram creation unit creates a plurality of chromatogram relating to a predetermined plurality of mass ranges;
  the processor is configured to cause, when at least any one signal intensity of the plurality of chromatograms reaches the predetermined upper limit after exceeding the predetermined lower limit, the timing determination unit to determine that point in time as the timing to perform MS/MS analysis for the respective mass range, and when the at least any one signal intensity reaches a top of a peak without reaching the upper limit after exceeding the lower limit, the timing determination unit to determine that point in time as the timing to perform MS/MS analysis for the respective mass range; and
  the MS analyzer performs MS/MS analysis that, among ions generated in the ionization unit, takes ions belonging to a mass range corresponding to a chromatogram that is used by the timing determination unit as precursor ions.

* * * * *